United States Patent [19]

Whiting

[11] Patent Number: 5,003,570
[45] Date of Patent: Mar. 26, 1991

[54] POWDER DIFFRACTION METHOD AND APPARATUS

[75] Inventor: Bruce R. Whiting, Pittsford, N.Y.

[73] Assignee: Eastman Kodak Company, Rochester, N.Y.

[21] Appl. No.: 438,477

[22] PCT Filed: Oct. 16, 1987

[86] PCT No.: PCT/US87/02669
§ 371 Date: Oct. 16, 1987
§ 102(e) Date: Oct. 16, 1987

[87] PCT Pub. No.: WO89/03526
PCT Pub. Date: Apr. 20, 1989

[51] Int. Cl.⁵ .......................................... G01N 23/207
[52] U.S. Cl. ......................................... 378/75; 378/76; 250/327.2
[58] Field of Search ...................... 378/70, 71, 73, 75, 378/76, 79, 81, 83; 250/327.2 E, 327.2 C

[56] References Cited

U.S. PATENT DOCUMENTS

| | | | |
|---|---|---|---|
| 2,539,196 | 1/1951 | Marshall | 378/75 |
| 3,903,415 | 9/1975 | Holzapfel | 378/75 |
| 4,015,125 | 3/1977 | Donnay et al. | |
| 4,076,981 | 2/1978 | Sparks et al. | |
| 4,217,493 | 8/1980 | Li et al. | |
| 4,301,364 | 11/1981 | Goebel | |
| 4,356,398 | 10/1982 | Komaki et al. | 250/327.2 B |
| 4,439,425 | 12/1984 | Borgonovi | |

OTHER PUBLICATIONS

Miyahara et al., Nuclear Instruments and Methods in Modern Physics Research, A246, (1986), 572-578.

*Primary Examiner*—Carolyn E. Fields
*Assistant Examiner*—David P. Porta
*Attorney, Agent, or Firm*—Thomas H. Close

[57] ABSTRACT

In a stimulable phosphor powder diffraction apparatus, a circularly symmetric diffraction pattern is recorded in the stimulable phosphor. The 2-D diffraction pattern is read out, and the resulting signal is processed to produce a 1-D signal representing the average of the 2-D diffraction pattern at points equidistant from the center of the diffraction pattern.

6 Claims, 3 Drawing Sheets

POWDER DIFFRACTION METHOD AND APPARATUS

TECHNICAL FIELD OF THE INVENTION

This invention relates to the detection and recording of diffraction patterns from powdered or amorphous materials, and in particular to detecting such diffraction patterns with a stimulable phosphor detector.

BACKGROUND OF THE INVENTION

It is well known that the scattering of incident radiation such as x-rays, gamma rays, cathode rays, etc. from a sample of material can yield information about the atomic structure of the material. When such a beam of radiation strikes a sample, a diffraction pattern of radiation strikes is created, which has a spatial intensity distribution that depends on the wavelength of the incident radiation and the atomic structure of the material. The following discussion will focus on x-ray powder diffraction as a nonlimiting example.

If the sample is an oriented single crystal, the diffraction pattern consists of a series of spots, corresponding to a projection of the reciprocal lattice of the crystal. If the molecules of the sample are randomly oriented (e.g. polycrystalline, amorphous, or powdered) the diffraction pattern becomes a series of cones, concentric with the incident beam, with the intensity and angle of the cone revealing information about the material structure. The study of diffraction patterns from powdered materials is generally referred to as powder diffraction. The function of a powder diffraction detector is to determine the angle and the intensity of this diffraction pattern.

Photographic film is one widely used detector for powder diffraction. When the film is exposed to x-rays, a latent image of the diffraction pattern is formed and when the film is developed, the density of the developed image is a measurement of the x-ray intensity in the diffraction pattern. If a flat sheet of film is placed perpendicular to the x-ray beam, the powder diffraction pattern image is a series of concentric circles. It is often desirable to record a wide diffraction angle, approaching 90 degrees. To accomplish this, in a so called Debeye-Scherrer camera, a strip of film is positioned on a cylindrical surface that intersects the beam, with the axis of the cylinder passing through the sample. The film strip records a portion of the diffraction pattern comprising arcs of the diffraction circles. While film has very good spatial resolution and can record large area patterns, it suffers from several drawbacks. Because film absorbs only a small percentage of the x-ray quanta incident on it and because it has a relatively high background noise in the form of chemical fog, film is a slow or insensitive detector of x-rays. I.e., high doses of x-rays must be given the sample to achieve a readable image with acceptable signal to noise ratio. While conventional x-ray intensifying screens can be employed to increase the sensitivity of film based powder diffraction systems, it is difficult to maintain intensity calibration with such screens. Film has a limited range of density linearity versus exposure, typically less than two orders of magnitude, so that widely differing intensities cannot be measured on the same piece of film. Also, film must be processed with wet chemistry which is an inconvenience. Finally, to utilize computers to analyze the data, the film must be scanned with a densitometer to convert densities to digital data, a time consuming intermediate step. Generally the scanning is performed on the film strip in a direction perpendicular to the arc segments of the diffraction pattern produced by the Debeye-Scherrer camera.

Various electronic detectors have been used to measure powder diffraction patterns, such as charge coupled devices, wire proportional counters, scintillators and the like. Such detectors efficiently absorb x-ray quanta and have little noise, so they are more sensitive than film, and produce digital electronic data directly. However, electronic detectors usually have a maximum counting rate so they cannot record strong intensities without dead time losses. Also, they have limited size so they can cover only a small area at one time. To form a complete scan the electronic detector must be moved until it has sequentially covered the entire area, resulting in additional exposure time. Recently, position sensitive detectors, which measure the position of quanta along a line instead of at a point, have been employed. Such position sensitive detectors must also be moved to cover an area.

The accumulation of accurate data for powder diffraction can take many hours or even days with conventional apparatus, this is a severe limitation on throughput when it is desirable to rapidly examine many samples.

Another technology for recording x-ray intensities is based on stimulable storage phosphors. Such storage phosphors when exposed to high energy radiation such as x-rays, cathode rays, etc., store a portion of the incident radiation. If the exposed phosphor is then exposed to stimulating radiation, such as visible light or heat, the phosphor will emit radiation in proportion to the stored energy of the original exposing radiation. Screens formed from such stimulable phosphors have been discussed in the literature (J. Miyahara et al., Nuclear Instruments and Methods in Modern Physics Research A246(1986), (572-578) as having very desirable properties, in terms of sensitivity and exposure latitude, for the detection of x-ray diffraction patterns from single crystal samples. Because stimulable phosphors efficiently absorb incident quanta and have very low background, they are 5-50 times more sensitive than photographic film. Stimulable phosphor x-ray imaging systems have resolutions on the order of 0.1 mm and can be made in large area formats, with millions of effective image sensing elements over a large area simultaneously integrating intensities, with no counting rate limitations. The stimulated signal is linearly related to the radiation exposure over at least 5 orders of magnitude. However, x-ray diffraction apparatus employing stimulable phosphors would improve the amount of exposure required only by the ratio of phosphor screen to film sensitivity. An even larger improvement is desirable.

SUMMARY OF THE INVENTION

The object of the present invention is to provide powder diffraction method and apparatus employing a stimulable phosphor detector capable of producing an exposure reduction improvement greater than a factor of 50, when compared to conventional film based powder diffraction apparatus and methods.

The object of the present invention is achieved by forming a latent image of a two dimensional circularly symmetric powder diffraction pattern in a stimulable phosphor sheet; reading the image out of the phosphor sheet in the form an image signal representing the two dimensional powder diffraction pattern, and processing the powder diffraction image signal to form a processed image signal representing a one-dimensional radial section of the two-dimensional circularly symmetric diffraction pattern by averaging the signal values representing points equidistant from the center of the circularly symmetric diffraction pattern.

In a preferred mode of practicing the present invention, a sheet of stimulable phosphor material is formed in the shape of a right circular truncated cone, with the axis of the cone aligned with beam of incident radiation directed at a powder sample, and the powder sample located near a plane defined by the base of the cone, thereby enabling the efficient detection of the diffraction pattern at angles up to 90 degrees.

In a further mode of practicing the invention, two such truncated cones of stimulable phosphor material arranged base to base are employed to detect both front and back scattered portions of the diffraction pattern.

In the preferred mode, the cone angle is 90 degrees, and a stimulable phosphor material is read out by rotating the cone about its axis, while stimulating and sensing the pattern of light entitled from the stimulable phosphor along lines defined by a plane passing through the axis of the cone.

BRIEF DESCRIPTION OF DRAWINGS

1.
FIG. 1 is a schematic diagram showing apparatus for reading out a latent image in a stimulable phosphor;
3.

DETAILED DESCRIPTION OF THE INVENTION

As used herein, "powder diffraction" refers to methods for producing diffraction patterns by irradiating materials that have a random structure. The powder diffraction pattern defines concentric cones whose axes are coincident with that of the incident beam of radiation. Examples of "powdered" material include those consisting of many small crystals, polycrystalline materials, and amorphous materials.

Figure 1:
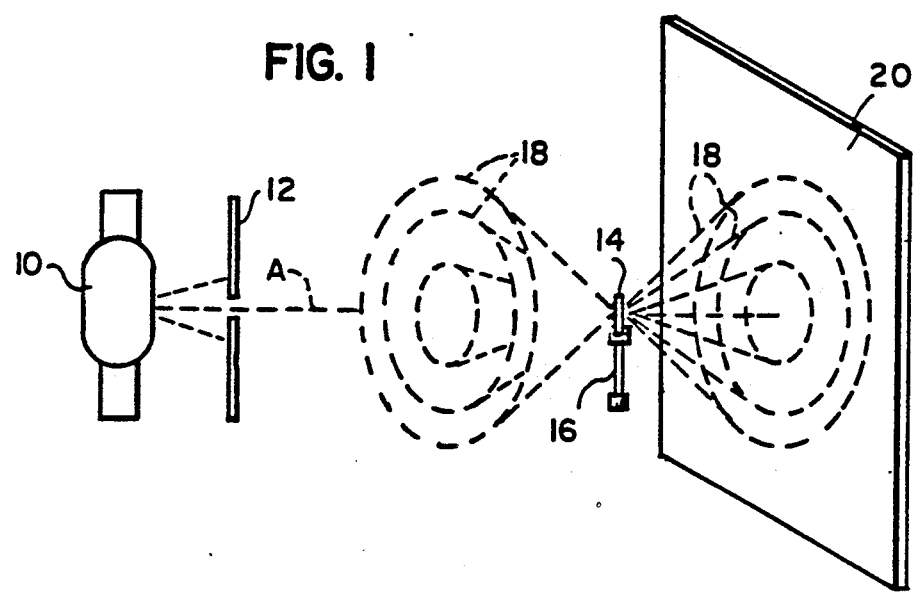
FIG. 1 is a schematic diagram showing apparatus for performing powder diffraction;
2.

The powder diffraction apparatus for exposing a stimulable phosphor sheet is generally shown in FIG. 1. A beam of incident x-radiation A is generated by an x-ray tube 10 and collimated by an aperture in plate 12. The beam A strikes a powder sample 14 in a sample holder 16, and the diffracted radiation scatters from the sample in a pattern of concentric cones 18. The scattering angles of interest include the forward (shown by dashed lines) and reverse (shown by solid lines) directions relative to the incoming beam, and can approach directions perpendicular to the beam. There is a minimum diffraction determined by the atomic structure of the powder sample of the powder sample, and the wavelength of incident radiation, determined by Braggs Law of diffraction. It is not necessary to collect data at angles less than this minimum, i.e., the detector need not record the undeflected beam (0 degrees) or angles less than the minimum angle.

The present invention will be first described in detail for an embodiment which is suitable for the detection of small angle scattering, i.e., detecting diffraction patterns with relatively small cone angles in the forward direction.

Figure 2:
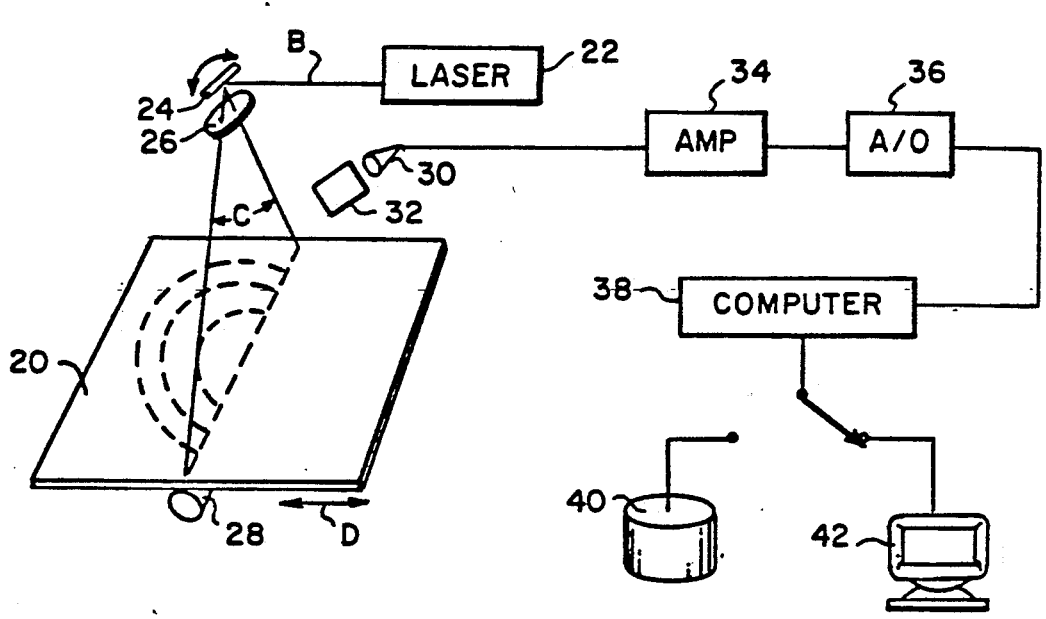

As shown in FIG. 1, a stimulable phosphor sheet 20 is placed in the path of the diffracted radiation perpendicular to the incident beam A. The latent image formed in the sheet 20 is a circularly symmetric pattern of concentric rings centered about the beam A. The stimulable phosphor sheet preferably comprises a stimulable phosphor as described in the above cited article of Miyahara et al, but other suitable stimulable phosphor materials may be employed. After exposure, the stimulable phosphor sheet 20 is moved to read out apparatus and the latent image of the diffraction pattern is read out by scanning the stimulable phosphor with a beam of stimulating radiation. As shown in FIG. 2, at the scanning station a beam B of stimulating radiation (e.g. infrared radiation) is generated, for instance by a laser source 22 and is deflected by a mirror deflector 24 to scan the beam B across the stimulable phosphor sheet. The beam B is focused by an appropriate optics 26 and is scanned across the stimulable phosphor sheet 20 in the direction indicated by arrow C. A translation mechanism 28 moves the stimulable phosphor sheet 20 in a direction indicated by arrow D perpendicular to the travel of the deflected beam, thereby performing a raster scan of the stimulable phosphor sheet. The intensity of the stimulated fluorescence from the stimulable phosphor sheet is detected to form a signal representing the two-dimensional powder diffraction pattern. The detector comprises photomultiplier tube 30 which receives light through an optical filter 32 which blocks stimulating wavelengths but passes the stimulated light. The signal from the photomultiplier tube 30 is electronically amplified and filtered by amplifier 34, and converted to a digital signal by an analog-to-digital (A/D) converter 36. The signal is processed according to the present invention in a digital computer 38, and can be stored on a storage medium, such as a magnetic tape or disc 40 or displayed on a display means such as CRT 42 or hardcopy printer.

Each data point represented by the powder diffraction image signal bears information about the intensity of the powder diffraction pattern, but also includes some uncertainty in its measurement due to noise from electronic sources, quantum statistics, background radiation, etc. The signal-to-noise ratio (SNR) of the data would normally be improved by increasing the radiation exposure, which results in longer exposure times, or by employing a more expensive x-ray source to produce a more powerful beam of x-rays.

According to the present invention, the SNR of the signal is improved by adding together, i.e., signal averaging, data points which correspond to the same parts of the diffraction pattern. The signal processing is accomplished in digital computer 38 by averaging together all data points equidistant from the incident beam, which is the center of the circularly symmetric diffraction pattern. This average value more accurately represents the intensity of the diffraction pattern than any one point, typically by an amount proportional to the square root of the number of points averaged. By using this average value the powder diffraction measurement achieves a more accurate result from a lower exposure. The processed signal represents the average intensity along a radius from the center of the diffraction pattern, which is converted into intensity versus diffraction angle, and is used to identify the atomic structure of the sample by comparison to known references. By employing the complete circle of the diffraction pattern to generate the final signal, the signal-to-noise ratio is optimized because all detected quanta are utilized.

Figure 3:
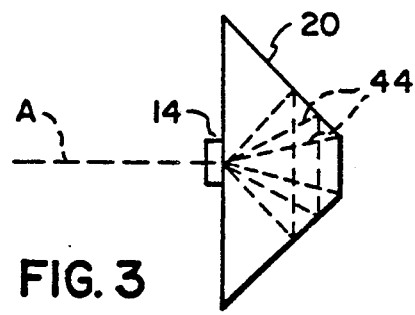
FIG. 3 is a schematic diagram showing a conical detector employed with the present invention;
4.
Figure 4:
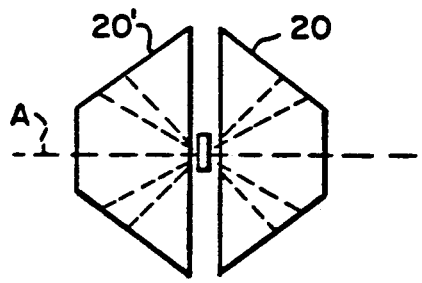
FIG. 4 is a schematic diagram showing a pair of conical detectors to detect both forward and reflected scattered radiation;
5.

The method described above is appropriate for small angle scattering. To increase the angular resolution of the apparatus, a larger angle needs to be subtended by the stimulable phosphor sheet 20. This may be accomplished either by moving the sheet 20 closer to the sample or by increasing the sheet size. The former solution suffers from reduced angular resolution since the finite resolution of the sheet subtends a larger angle as it is brought closer to the sample, and the latter solution suffers from the requirement of a larger screen area to be scanned in the read out apparatus. Neither solution works in the limit of data at angles of 90 degrees to the incident beam. Therefore, according to a preferred embodiment of the present invention, the storage phosphor screen 20 is formed into the shape of a truncated conical surface, placed such that the cone axis is coincident with the radiation beam A. FIG. 3 is a cross section view of such a conical detector. With the conical detector arranged as described above, the cones of the diffraction pattern intercept the storage phosphor surface to form a latent image composed of circles perpendicular to the detector axis at various distances from the sample. This conical collector shape can record diffracted radiation at angles up to and exceeding 90 degrees with no resolution loss and with minimal increase in the area of the screen which must be scanned to produce the signal. To capture both forward and reflected scattering, two cones of stimulable phosphor sheet material 20 and 20' are employed one on either side of the sample 14 as shown in FIG. 4.

Figure 5:
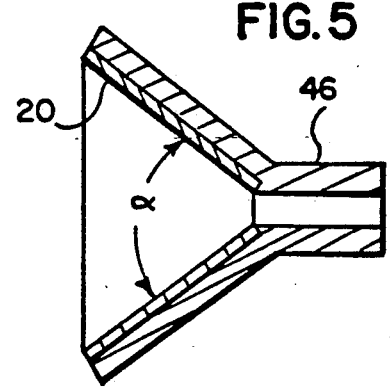
FIG. 5 is a cross sectional view of a conical detector;
6.
Figure 6:
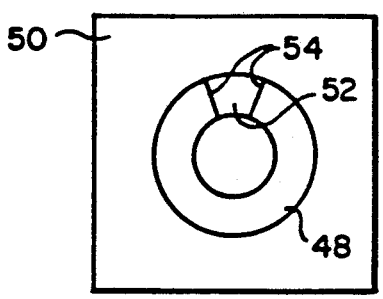
FIG. 6 is a schematic diagram showing how an annulus of phosphor material is cut from a sheet for lining the conical detector of FIG. 5;
7.

Shown in FIG. 5 the conical detector is formed by coating the inside of a conical support 46 with phosphor material 20. Alternatively, an annulus 48 is cut from a sheet of flexible stimulable phosphor material 50 as shown in FIG. 6. A radial section 52 of the annulus is removed and the edges 54 are joined to form a truncated cone. This cone of material is held in a holder similar to the holder 46 shown in FIG. 5. To maintain high resolution while minimizing surface area, a cone angle $\alpha$ of 90 degrees is preferable.

Figure 7:
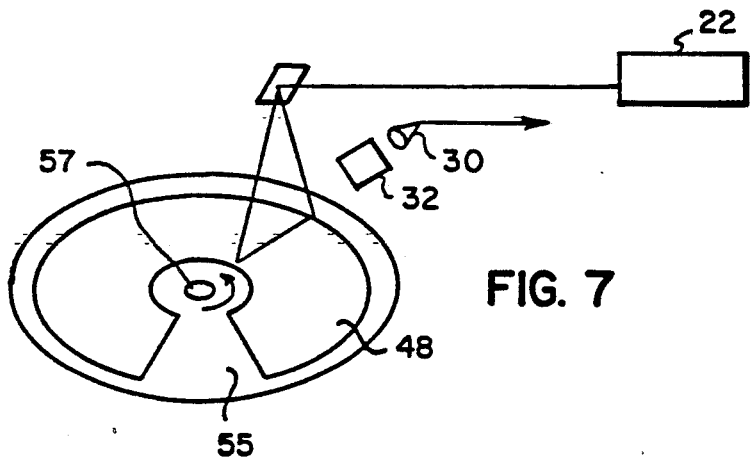
FIG. 7 is a schematic diagram illustrating an alternative method of reading out a latent image from a stimulable phosphor;
8.

After exposure, the latent image formed in a stimulable phosphor sheet in a conical detector can be read out in several ways. If a flexible sheet is used, the sheet is removed and laid flat, and scanned by a flatbed scanner of the type shown in FIG. 2. Alternatively, the flat annular segment 48 of stimulable phosphor material is mounted on a turntable 55 as shown in FIG. 7, with the center of the diffraction pattern coincident with the center 57 of the turntable 55. The turntable 55 rotates while the stimulable phosphor sheet is stimulated one radial line at time. The signal is processed to average the signal around each point equidistant from the center of the diffraction pattern as described above.

Figure 8:
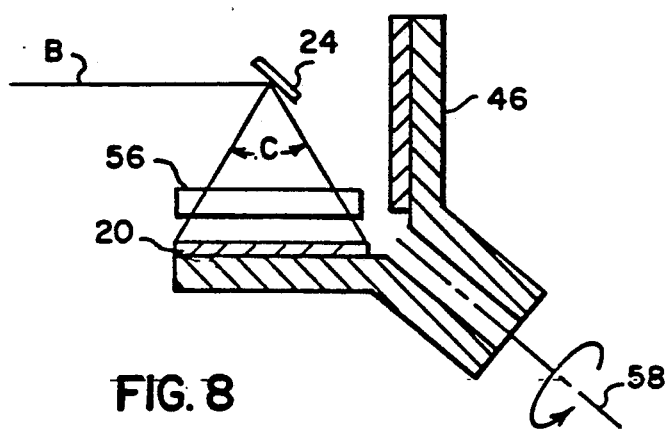
FIG. 8 is a schematic diagram illustrating read out of the latent image in a conical detector;
9.

Alternatively the conical detector is scanned directly as shown in FIG. 8. by deflecting a stimulating beam B along the surface of cone 20 following a line segment described by the intersection of a plane containing the cone axis and the conical surface. Stimulated radiation is sensed by a light detector 56. After the scan of each line segment, the cone holder 46 is rotated about its axis 58 to present a new line segment for scanning. The signal from corresponding positions along each line are averaged together as described above to generate the processed powder diffraction pattern signal.

Figure 9:
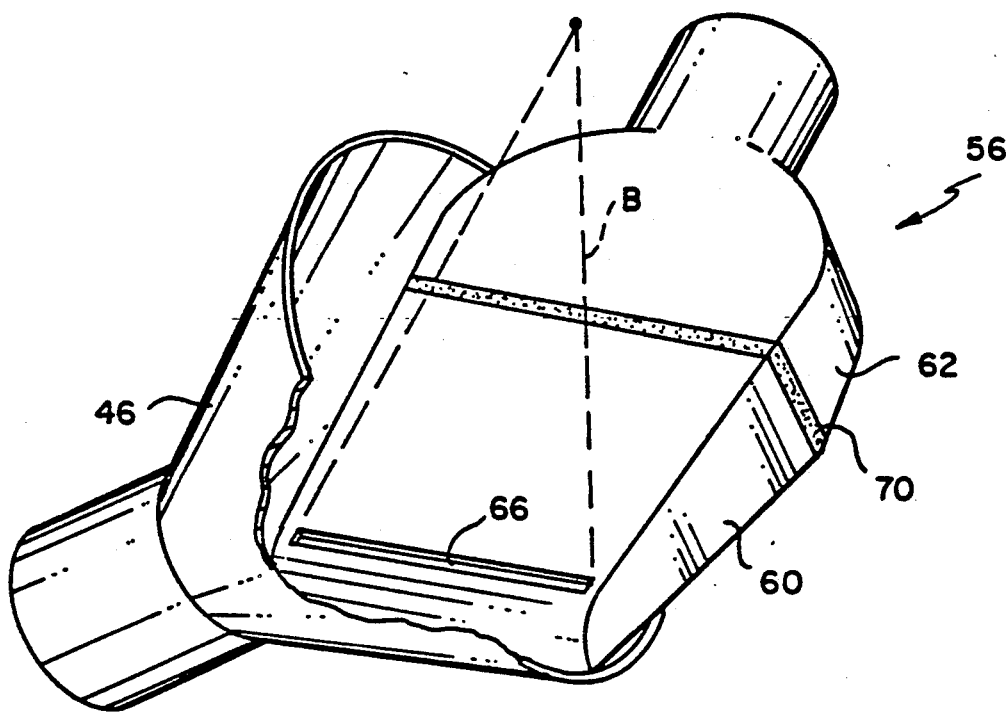
FIG. 9 is a perspective view, partially broken away showing the apparatus schematically shown in FIG. 8.
Figure 10:
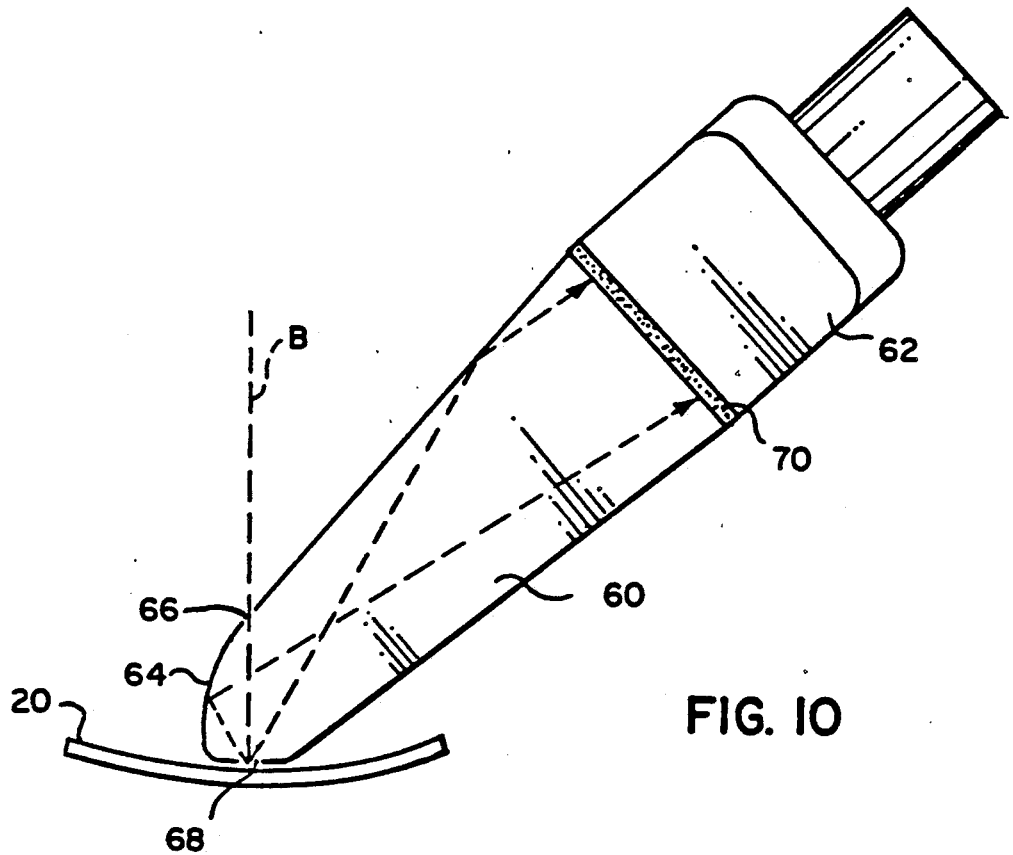
FIG. 10 is a side view of the light detector shown in FIG. 9.

A preferred embodiment of light detector 56 is shown in FIG. 9. The light detector includes a mirror box light collector 60, and a photomultiplier tube 62. The photomultiplier tube 62 has a rectangular light receiving face of 2.5×7.5 cm and it is of the type that can be purchased from the Hamamatsu Company Part No. 1612. The mirror box 60 is a tapered rectangular mirror box having an elliptical reflector 64 on one end. A side view of the light detector 56 is shown in FIG. 10. The light collector 60 defines a slit 66 and a slit 68 for passing the beam of stimulating radiation to the surface of the phosphor material and for collecting the admitted light. The light detector includes a filter 70 for absorbing stimulating radiation and passing the emitted radiation.

In the preferred embodiment, the truncated cone of stimulable phosphor material is a right circular cone having an angle $\alpha$ of 90 degrees, a base diameter of 14 cm and a height of 11 cm.

COMPARATIVE EXAMPLES

1. A sample of powdered Al O was placed in a Debeye-Scherrer camera having a radius of 5.65 cm and exposed with a beam of x-rays from a Cu K line at 40 kV and 25 mA. Using a strip of 35 mm photographic film for two hours. The film was developed and scanned in a direction perpendicular to the diffraction pattern, yielding a one dimensional powder diffraction pattern. The diffraction pattern had a signal to noise ratio of 88 measured by determining a base line for a prominent peak, measuring the area under the peak, and dividing by the standard deviation of the base line.

2. The Debeye-Scherrer camera was replaced by a sheet of stimulable phosphor material of the type disclosed in the Miyahara et al article, arranged as shown in FIG. 1 and exposed by the x-ray beam for one minute. The stimulable phosphor sheet was read out in a flatbed scanner of the type shown in FIG. 2, and the signal was digitized. The signal resulting from a single scan along a radius of the diffraction pattern was extracted from the scanned data. The signal-to-noise ratio of the signal, determined as described above was about 3.

3. The total signal produced in example 2 was processed according to the present invention to form the signal representing the average of all points equidistant from a center point of the diffraction pattern. The signal processing was performed by a programmed general purpose digital computer. The computer program for performing the signal processing written in the fortran language, is included as Appendix A. The resulting one-dimensional diffraction pattern had a signal to noise ratio of 162, calculated as described above. Based upon the respective exposures and signal-to-noise ratios achieved in the comparative examples noted above, it is estimated that an exposure reduction factor of between 50 and 250 is achievable by the methods and apparatus according to the present invention.

INDUSTRIAL APPLICABILITY AND ADVANTAGES

The present invention is useful in powder diffraction, and has the advantage of producing a powder diffraction signal having higher signal-to-noise ratio employing lower exposure than prior art methods and apparatus.

| APPENDIX A Program CIRCL |
|---|
| C    PROGRAM TO AVERAGE PIXELS AS .FUNCTION OF RADIUS FROM ORIGIN |
| C    IYC,IXC are center of the diffraction pattern |
|      DO 1600 |
|        READ DISK(DATA,LIN,PIXSTR) ! A LINE OF PIXELS IS READ FROM DISK |
|        Do 1400 K=1,Npix |
|        R=(LIN−IYC)2+(PIXSTR+K−1−IXC)2 |
|        R=SQRT(R) |
|        IR=INT(R) |
|        DR=R−INT(R) |
|          AVE(IR+1) = Ave(IR+1) +(1−DR)*Data(Pixstra+K−1) |
|          AVE(IR+1) = AVE(IR+2)+ DR*DATA(PIXSTR=K−1) |
|          WR(IR+1)=WR(IR+1)+1−DR |
|          WR(IR+2)=WR(IR+2)+DR |
| 1400    Continue |
| 1600    CONTINUE |
| C    Average data |
| C |
| C    OUTPUT NORMALIZED RESULTS |
|      Do 2300 K=1, MAXR |
|      Write(6,*)K−1,Ave(K)/WR(K) |
| 2300    Continue |
|      End |

I claim:

1. Powder diffraction apparatus comprising:
  a. means for producing a beam of incident radiation;
  b. means for positioning a powder sample in said beam to generate a powder diffraction pattern composed of concentric cones of diffracted radiation;
  c. a sheet of stimulable phosphor material located to receive the diffracted radiation to produce a two-dimensional circularly symmetric latent image of the diffraction pattern centered about said beam;
  d. means for reading out the latent image from the stimulable phosphor sheet to generate an image signal representing the two-dimensional diffraction pattern, said means for reading out the latent image comprising means for producing a beam of stimulating radiation, means for scanning the beam of stimulating radiation along a radius of the circularly symmetric latent image pattern, means for collecting and detecting radiation emitted from the stimulable phosphor to produce an electrical signal representing the intensity of the emitted radiation along said radius, and means for providing a relative rotation between said sheet of stimulable phosphor material and said scanning and collecting means about the center of circular symmetry of said latent image; and
  e. signal processing means responsive to said image signal for producing a processed image signal representing the average of the diffraction pattern at points equidistant from the center of the diffraction pattern.

2. The apparatus claimed in claim 1, wherein said stimulable phosphor material is sensitive to x-radiation to form a latent image, and sensitive to infrared radiation to release the latent image in the form of visible light; said incident radiation is x-radiation, and said stimulating radiation is infrared radiation; and said means for collecting and detecting, collects and detects visible light.

3. Powder diffraction apparatus comprising:
  a. means for producing a beam of incident radiation;
  b. means for positioning a powder sample in said beam to generate a powder diffraction pattern composed of concentric cones of diffracted radiation;
  c. a sheet of stimulable phosphor material located to receive the diffracted radiation to produce a two-dimensional circularly symmetric latent image of the diffraction pattern centered about said beam, said sheet of stimulable phosphor material being formed in the shape of a truncated cone having a conical axis coincident with said beam, said sample being located near a plane defined by the base of said cone;
  d. means for reading out the latent image from the stimulable phosphor sheet to generate an image signal representing the two-dimensional diffraction pattern; and
  e. signal processing means responsive to said image signal for producing a processed image signal representing the average of the diffraction pattern at points equidistant from the center of the diffraction pattern.

4. The apparatus claimed in claim 3, wherein said truncated cone is a right circular cone having a cone angle of 90 degrees, a base radius of 14 cm and a height of 11 cm.

5. The apparatus claimed in claim 3, further including a second sheet of stimulable phosphor material formed in a second truncated cone, located with its conical axis coincident with the beam and its base adjacent to the base of said first cone.

6. A powder diffraction method comprising the steps of:
  a. producing a beam of incident radiation;
  b. placing a powder sample in the beam to form a powder diffraction pattern;
  c. detecting the powder diffraction pattern with a sheet of stimulable phosphor material located to form a circularly symmetrical two-dimensional latent image centered on said beam;
  d. reading the latent image out of the stimulable phosphor material to produce a signal representing the two dimensional diffraction pattern image, said reading step comprising producing a beam of stimulating radiation, scanning the beam along a radius of the circularly symmetric latent image pattern, collecting and detecting radiation emitted from the stimulable phosphor to produce an electrical signal representing the intensity of the emitted radiation along said radius, and rotating said sheet of stimulable phosphor material about the center of circular symmetry of said latent image; and
  e. processing said signal to produce a processed signal representing a one dimensional radial section of said two dimensional image obtained by averaging the intensity of the diffraction pattern at points equidistant from the center of said pattern.

* * * * *